United States Patent [19]

Yasukawa

[11] Patent Number: 5,215,941
[45] Date of Patent: Jun. 1, 1993

[54] PROCESS FOR PRODUCING A SINTERED APATITE ARTICLE HAVING A POROUS SURFACE USING AN ACIDIC BUFFER SOLUTION

[75] Inventor: Fumie Yasukawa, Tokyo, Japan

[73] Assignee: Asahi Kogaku Kogyo K.K., Tokyo, Japan

[21] Appl. No.: 821,903

[22] Filed: Jan. 15, 1992

Related U.S. Application Data

[63] Continuation of Ser. No. 610,677, Nov. 8, 1990, abandoned.

[30] Foreign Application Priority Data

Nov. 10, 1989 [JP] Japan ................................ 1-293723

[51] Int. Cl.$^5$ .............................................. C04B 38/04
[52] U.S. Cl. .......................................... 501/1; 501/80; 156/667; 264/42; 264/43; 264/60
[58] Field of Search ....................... 501/1, 80; 156/656, 156/657; 264/42, 43, 60

[56] References Cited

U.S. PATENT DOCUMENTS

| | | | |
|---|---|---|---|
| 4,654,314 | 3/1987 | Takagi et al. | 501/1 X |
| 4,794,046 | 12/1988 | Nagai | 501/1 X |
| 4,919,751 | 4/1990 | Sumita et al. | 501/1 X |
| 5,017,518 | 5/1991 | Hirayama et al. | 501/1 |

FOREIGN PATENT DOCUMENTS

| | | |
|---|---|---|
| 61-213056 | 9/1986 | Japan . |
| 62-297284 | 12/1987 | Japan . |
| 64-45795 | 2/1989 | Japan . |
| 64-72978 | 3/1989 | Japan . |

OTHER PUBLICATIONS

Proceedings of the International Institute for the Science of Sintering (ISS) Symposium held in Tokyo, Japan Nov. 4–6, 1987, vol. 2, pp. 1332–1337.

DeWith et al, "Preparation, Microstructure and Mechanical Properies of Dense Polycrystalline Hydroxyapatite", J. of Mat. Sci. 16 (1981) pp. 1592–1598.

Primary Examiner—Karl Group
Attorney, Agent, or Firm—Sughrue, Mion, Zinn, Macpeak & Seas

[57] ABSTRACT

A process for producing a sintered apatite article having a porous surface by contacting a dense sintered apatite article with an acidic buffer solution, provided that the acidic buffer solution does not contain phosphoric acid.

7 Claims, 4 Drawing Sheets

PROCESS FOR PRODUCING A SINTERED APATITE ARTICLE HAVING A POROUS SURFACE USING AN ACIDIC BUFFER SOLUTION

This is a continuation of application Ser. No. 07/610,677 filed Nov. 8, 1990 now abandoned.

FIELD OF THE INVENTION

The present invention relates to a sintered apatite article having a porous surface (hereinafter often referred to "surface-porous sintered apatite article") and also to a process for producing the surface-porous sintered apatite article.

BACKGROUND OF THE INVENTION

JP-A-61-213056 discloses a method for forming a porous ceramic film on a ceramic substrate plate. The term "JP-A" as used herein means an "unexamined published Japanese patent application". In this method, calcium phosphate prepared by the wet process is precalcined at about 500° to 1,000° C. to prepare powder, subsequently a part of the raw powder is mixed with a binder and formed into a shaped article having a predetermined shape and the balance of the powder is mixed with another binder to provide a slurry, and then the slurry is coated on the above-obtained shaped article, followed by being dried and calcined. However, this method is disadvantageous because the production cost is high due to the use of the binders.

Further, JP-A-62-297284 discloses a method of forming a calcium phosphate film by flame spraying. This method, however, is defective in that the bonding strength of the film to the substrate is low and pore diameter is difficult to control.

SUMMARY OF THE INVENTION

Accordingly, an object of the present invention is to provide a sintered apatite article in which the surface thereof is porous and the central part thereof is dense.

Another object of the present invention is to provide a process for producing such a sintered article efficiently at a low cost by an extremely simple procedure.

Other objects and effects of the present invention will be apparent from the following description.

The present invention relates to a sintered apatite article having a porous surface which is obtained by the process comprising the step of: contacting a dense sintered apatite article with an acidic buffer solution, provided that the acidic buffer solution does not contain phosphoric acid.

DETAILED DESCRIPTION OF THE INVENTION

Figure 1:
FIG. 1 is an electron micrograph (magnification: 1,000) illustrating the structure of the surface of a sintered apatite article of the present invention obtained in Example 1 through 1-hour dipping.

The dense sintered apatite article used for producing the surface-porous sintered apatite article of the present invention may be composed of at least one apatite selected from the group consisting of hydroxyapatite, fluoroapatite, and chloroapatite. In the case where the dense sintered apatite article is composed of two or more apatites, the whole sintered article may be composed of a mixture of two or more apatites or only the surface of the sintered article may be composed of a different kind of apatite. Examples of the latter case include a sintered article obtained by subjecting a dense sintered hydroxyapatite article to a chemical treatment to convert the surface of the sintered article to fluorapatite.

The dense sintered apatite article to be used for producing the surface-porous sintered apatite article of the present invention can be obtained by any conventional methods as described, e.g., in *Proceedings of the International Institute for the Science of Sintering (IISS) Symposium*, vol.2, pp.1332-1337 (1987), *J. Mater. Sci.*, vol.16, pp.1592-1598 (1981), and U.S. Pat. No. 4,097,935. For example, a method may be employed, in which powder or a slurry of apatites manufactured by conventional processes are formed into a desired shape and then sintered. A method for shaping the apatite are not particularly limited, and either a dry or wet shaping method may be employed. For example, casting, extrusion, injection molding, compression molding, or the like can be used. The sintering is carried out generally at from 700° to 1,400° C., preferably at from 900° to 1,200° C. for from 2 to 4 hours.

A method for contacting the dense sintered apatite article with the buffer solution is not particularly limited, and is preferably by dipping.

Examples of the acidic buffer solution that can be used to produce the surface-porous sintered apatite article of the present invention include a citric acid based buffer solution, a hydrochloric acid based buffer solution, a phthalic acid based buffer solution, and the like, but any buffer solution other than those containing phosphoric acid may be used. The acidic buffer solution preferably has a pH of 6.0 or less, more preferably from 2.2 to 6.0, and particularly preferably from 2.2 to 3.5.

Specific examples of the acidic buffer solution used in the present invention include Clark-Lubs' buffer solution, Sorensen's buffer solution, Klthoff's buffer solution, Michaelis, buffer solution, Atkins-Pantin's buffer solution, Palitzsch's buffer solution, Menzel's buffer solution and Walpole's buffer solution that do not contain phosphoric acid.

By dipping the dense sintered apatite article as described above in an acidic buffer solution, a surface-porous sintered apatite article according to the present invention is obtained. The time period for the dipping varies, depending on the pH of the buffer solution used. According to the desired surface porosity, the pH of the buffer solution and the dipping time are suitably determined. In order to produce a dense sintered apatite article having a porous surface, the dipping time is generally about 10 minutes or more at a pH of 2.2, about 30 minutes or more at pH 3.0, and about 20 hours or more at pH 6.0. The sintered apatite article is then withdrawn from the buffer solution at the time when the desired porous surface is obtained. If the dipping time is prolonged, the size of the sintered apatite is reduced by dissolving while maintaining the porous surface thereof.

Although the mechanism of only the surface layer of the dense sintered apatite article being made porous but not etched uniformly by contacting with the buffer solution for a predetermined period has not yet been elucidated completely, it can be considered that the buffer solution exerts a relatively mild dissolving action, and dissolution takes place first at grain boundaries, from which the dissolution proceeds. There is a tendency that the longer the contacting time, the smaller the number of minute pores and the coarser the pores.

According to the method of the present invention, a sintered apatite article whose surface is porous can be produced extremely easily and efficiently at a low cost. Because of its structure in which the surface portion is porous and the inner part is dense, the sintered apatite article of the present invention has an extremely high strength. Further, due to the highly active porous apatite layer in the surface portion, the sintered apatite article of the present invention is useful as an adsorbent, a separating material, a biomaterial such as a bone prosthesis, a bioreactor, a sensor, etc.

The present invention is explained below in more detail by reference to the Examples, which should not be construed as limiting the scope of the present invention.

EXAMPLE 1

A slurry of hydroxyapatite prepared by the conventional wet process and having a Ca/P molar ratio of 1.67 was spray dried to obtain powder of the apatite. This powder was compacted with a hydrostatic press at 196 MPa. The resulting powder compact was sintered at 1,050° C. for 4 hours to prepare a dense sintered cylindrical article having a diameter of 5 mm and a length of 20 mm. The dense sintered article obtained was then dipped for 1 hour in a 0.1M citric acid buffer solution containing citric acid and sodium citrate and having a pH of 3.0, and dried. The surface of the thus-treated sintered article was examined with an electron microscope, and an electron micrograph (magnification: 1,000) of the surface is shown in FIG. 1.

Figure 2:
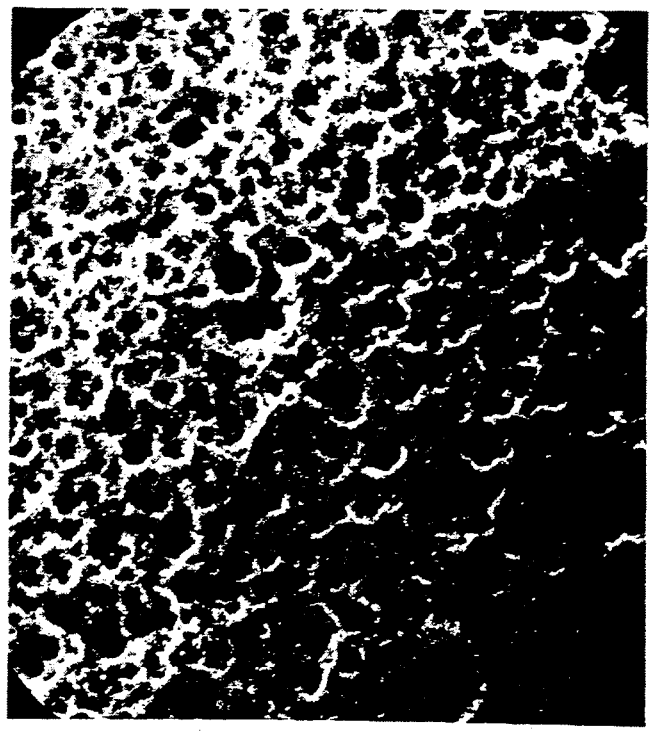
FIG. 2 is an electron micrograph (magnification: 400) illustrating the structure of the surface of a sintered apatite article of the present invention obtained in Example 1 through 48-hour dipping.

Furthermore, the same dense sintered article as that treated above was dipped in the same buffer solution for 48 hours. An electron photomicrograph (magnification: 400) of the surface of the resulting sintered article is shown in FIG. 2.

The untreated dense sintered article and the sintered article treated by 48-hour dipping were examined for three-point bending strength by the following manner: A cylindrical article having a diameter of 5 mm and a length of 21 mm was placed on two pedestals disposed at an interval of 17 mm, and a load was applied to the article at the center of the pedestals. The results obtained are shown in Table 1 below.

TABLE 1

| | (Three-point bending strength) | | |
|---|---|---|---|
| | Average $(kg/cm^2)$ | Maximum $(kg/cm^2)$ | Minimum $(kg/cm^2)$ |
| Untreated article | 2,600 | 3,400 | 1,900 |
| 48-Hour dipped article | 2,020 | 2,480 | 1,100 |

The results in Table 1 indicate that although the strength has been lowered to some degree by dipping in the acidic buffer, the thus-treated sintered article is sufficient to withstand practical use because the average of the strength thereof is above the level of 2,000 $kg/cm^2$, which is equal to that of ordinary dense sintered products.

EXAMPLE 2

Figure 3:
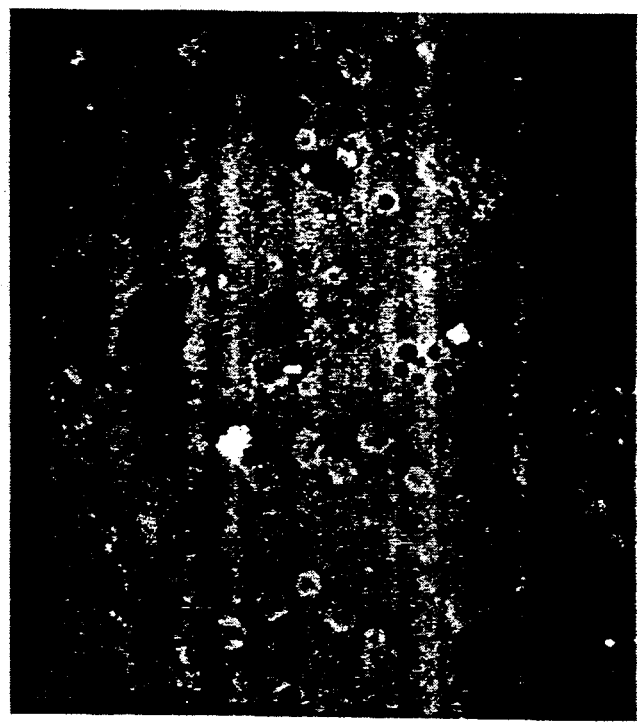
FIG. 3 is an electron micrograph (magnification: 400) illustrating the structure of the surface of a sintered apatite article of the present invention obtained in Example 2 through 1-hour dipping.
Figure 4:
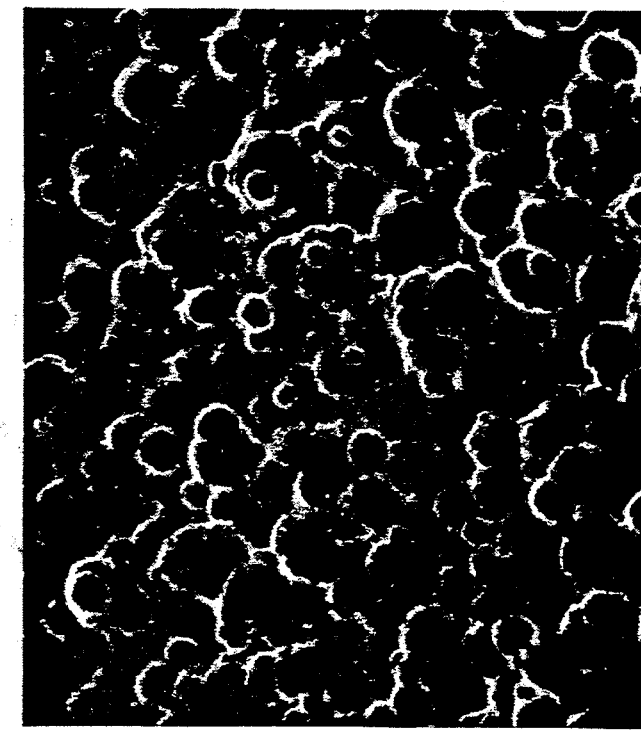
FIG. 4 is an electron micrograph (magnification: 400) illustrating the structure of the surface of a sintered apatite article of the present invention obtained in Example 2 through 24-hour dipping.

The dense sintered hydroxyapatite articles prepared in the same manner as in Example 1 were dipped in a 0.2M hydrochloric acid buffer solution containing hydrochloric acid and sodium hydrogen phthalate and having a pH of 2.2 for 1 hour and for 24 hours, and then dried. The surface of each of the thus-treated sintered articles was examined with an electron microscope, and electron micrograph (magnification: 400) thereof are shown in FIGS. 3 and 4, respectively.

EXAMPLE 3

The dense sintered hydroxyapatite articles prepared in the same manner as in Example 1 were dipped in a 0.1M citric acid buffer solution containing citric acid and sodium citrate and having a pH of 6.0 for 1 week, and then dried. The surface of the thus-treated sintered article was examined with an electron microscope, and electron micrograph (magnification: 400) thereof is shown in FIG. 5.

COMPARATIVE EXAMPLE 1

The same procedures as in Example 1 were repeated except that $10^{-3}N$ hydrochloric acid solution (pH 3.0) was used in place of the citric acid buffer solution. The surfaces of the resulting sintered articles were examined with an electron microscope. An electron micrograph (magnification: 1,000) of the surface of the sintered article which had undergone 1-hour dipping in the hydrochloric acid solution is shown in FIG. 6, while an electron micrograph (magnification: 1,000) of the surface of the sintered article which had undergone 24-hour dipping is shown in FIG. 7.

Figure 5:
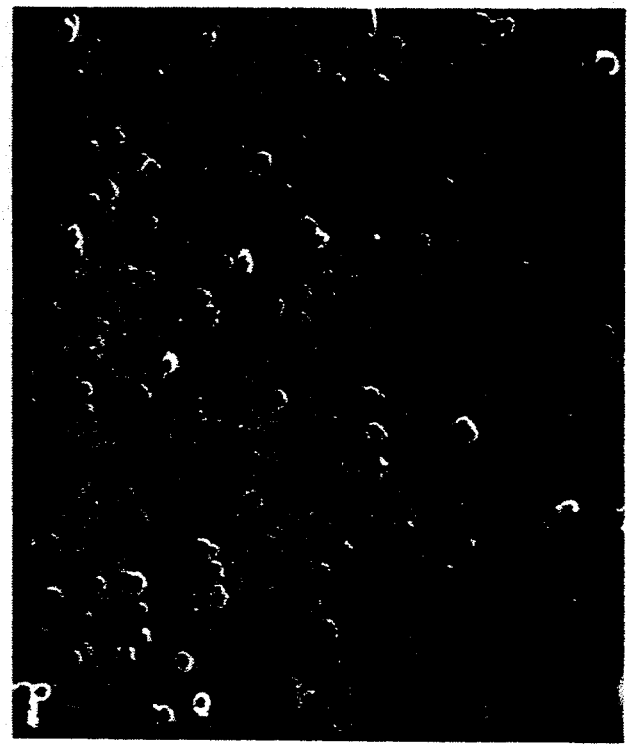
FIG. 5 is an electron micrograph (magnification: 400) illustrating the structure of the surface of a sintered apatite article of the present invention obtained in Example 3 through 1-week dipping.
Figure 6:
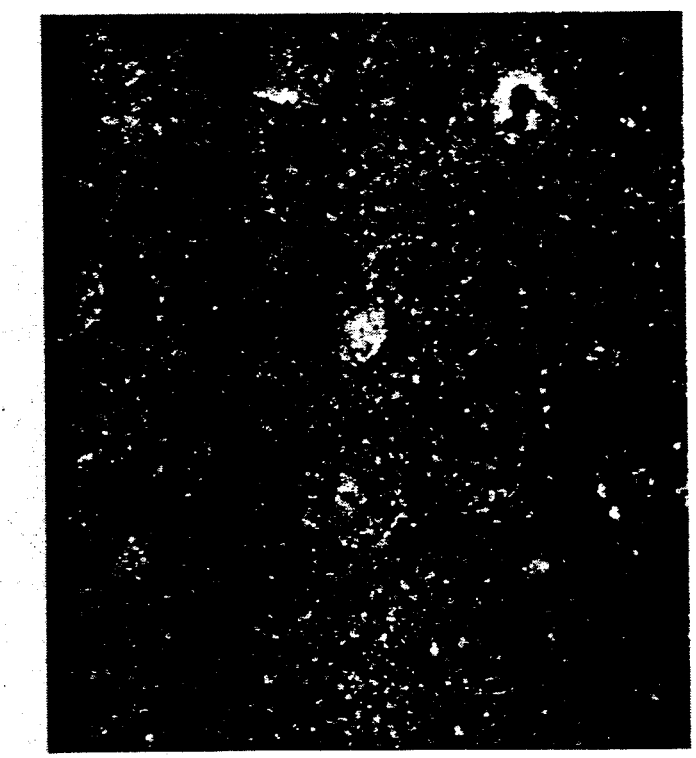
FIG. 6 is an electron micrograph (magnification: 1,000) illustrating the structure of the surface of a sintered apatite article obtained in Comparative Example 1 through 1-hour dipping.
Figure 7:
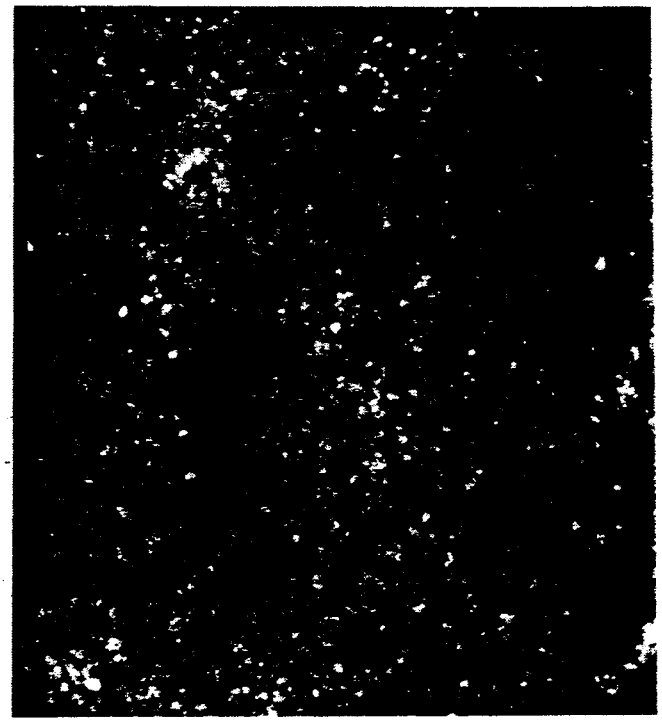
FIG. 7 is an electron micrograph (magnification: 1,000) illustrating the structure of the surface of a sintered apatite article obtained in Comparative Example 1 through 24-hour dipping.

In Examples 1 to 3, the articles shown in FIGS. 2, 4 and 5 each had a porous surface by the action of the buffer solution, but in Comparative Example 1, the articles shown in FIGS. 6 and 7 had no porous surface and the surface was uniformly etched by the acid solution.

While the invention has been described in detail and with reference to specific embodiments thereof, it will be apparent to one skilled in the art that various changes and modifications can be made therein without departing from the spirit and scope thereof.

What is claimed is:

1. A process for producing a sintered article having a porous surface, which sintered article consists essentially of apatite, which comprises the step of:

contacting a dense sintered article, which sintered article consists essentially of apatite, with an acidic buffer solution, provided that said acidic buffer solution does not contain phosphoric acid.

2. A process as claimed in claim 1, wherein said acidic buffer solution has a pH of 6.0 or less.

3. A process as claimed in claim 2, wherein said acidic buffer solution has a pH of from 2.2 to 6.0.

4. A process as claimed in claim 3, wherein said acidic buffer solution has a pH of from 2.2 to 3.5.

5. A process as claimed in claim 1, wherein said dense sintered apatite article consists essentially of at least one apatite selected from the group consisting of hydroxyapatite, fluoroapatite, and chloroapatite.

6. A process as claimed in claim 1, wherein said acidic buffer solution is selected from the group consisting of a citric acid based buffer solution, a hydrochloric acid based buffer solution, and a phthalic acid based buffer solution.

7. A process as claimed in claim 1, wherein the apatite constituting the dense sintered article has a Ca/P molar ratio of 1.67.

* * * * *